United States Patent
Paul

(10) Patent No.: US 12,033,323 B2
(45) Date of Patent: Jul. 9, 2024

(54) METHOD, DEVICE AND COMPUTER-READABLE MEDIUM FOR AUTOMATICALLY CLASSIFYING CORONARY LESION ACCORDING TO CAD-RADS CLASSIFICATION BY A DEEP NEURAL NETWORK

(71) Applicant: SPIMED-AI, Paris (FR)

(72) Inventor: Jean-François Paul, Bourg-la-Reine (FR)

(73) Assignee: SPIMED-AI, Paris (FR)

( * ) Notice: Subject to any disclaimer, the term of this patent is extended or adjusted under 35 U.S.C. 154(b) by 312 days.

(21) Appl. No.: 17/613,455

(22) PCT Filed: May 18, 2020

(86) PCT No.: PCT/EP2020/063798
§ 371 (c)(1),
(2) Date: Nov. 22, 2021

(87) PCT Pub. No.: WO2020/234233
PCT Pub. Date: Nov. 26, 2020

(65) Prior Publication Data
US 2022/0215541 A1    Jul. 7, 2022

(30) Foreign Application Priority Data

May 23, 2019   (FR) ...................................... 1905408

(51) Int. Cl.
| | |
|---|---|
| *G06T 7/00* | (2017.01) |
| *A61B 6/00* | (2024.01) |
| *A61B 6/03* | (2006.01) |
| *A61B 6/50* | (2024.01) |
| *G06N 3/04* | (2023.01) |

(Continued)

(52) U.S. Cl.
CPC ............ *G06T 7/0012* (2013.01); *A61B 6/032* (2013.01); *A61B 6/503* (2013.01); *A61B 6/504* (2013.01);

(Continued)

(58) Field of Classification Search
CPC ......... G06T 7/0012; G06T 2207/10081; G06T 2207/10116; G06T 2207/30008; G06T 2207/30101; G06V 10/761
See application file for complete search history.

(56) References Cited

U.S. PATENT DOCUMENTS

2010/0239140 A1* 9/2010 Ruijters .................. G06T 19/00
382/130

FOREIGN PATENT DOCUMENTS

WO    2019025270 A1    2/2019

OTHER PUBLICATIONS

Szilveszter et al, "Structured reporting platform improves CAD-RADS assessment", 2017, Journal of Cardiovascular Computed Tomography 11, pp. 449-454 (6 pages) (Year: 2017).*

(Continued)

*Primary Examiner* — David F Dunphy
(74) *Attorney, Agent, or Firm* — Maier & Maier, PLLC

(57) ABSTRACT

A computer-implemented method for determining the presence of a coronary lesion for a patient, including a first step of receiving at least one curvilinear or stretched multiplanar medical CT image of a coronary artery of the patient. The method further includes a step of determining a CAD-RADS (Coronary Artery Disease—Reporting and Data System value) classification value of a coronary lesion on the image or on a part of the image by using a first trained deep neural network applied directly to the detected images or parts of images.

17 Claims, 3 Drawing Sheets

(51) Int. Cl.
G06N 3/045 (2023.01)
G16H 30/40 (2018.01)
G16H 50/20 (2018.01)

(52) U.S. Cl.
CPC ............ *A61B 6/507* (2013.01); *A61B 6/5217* (2013.01); *G06N 3/045* (2023.01); *G16H 30/40* (2018.01); *G16H 50/20* (2018.01); G06T 2207/10081 (2013.01); G06T 2207/20084 (2013.01); G06T 2207/30048 (2013.01); G06T 2207/30096 (2013.01); G06T 2207/30101 (2013.01); G06T 2207/30168 (2013.01)

(56) References Cited

OTHER PUBLICATIONS

Von Knebel et al, "Coronary CT angiography-derived plaque quantification with artificial intelligence CT fractional flow reserve for the identification of lesion-specific ischemia," 2018, European Radiology 29, pp. 2378-2387 (10 pages) (Year: 2018).*

Von Knebel Doeberitz et al., "Coronary CT angiography-derived plaque quantification with artificial intelligence CT fractional flow reserve for the identification of lesion-specific ischemia," European Radiology, 2018, vol. 29, 11 pages.

Zreik et al., "Automatic Detection and Characterization of Coronary Artery Plaque and Stenosis using a Recurrent Convolutional Neural Network in Coronary CT Angiography", 2018, 14 pages.

Cano-Espinosa et al., "Automated Agatston Score Computation In Non-ECG Gated CT Scans Using Deep Learning", Progress In Biomedical Optics And Imaging, SPIE, 2018, vol. 10574, 9 pages.

Nakanishi et al., "Automated estimation of image quality for coronary computed tomographic angiography using machine learning", Eur Radiol, 2018, 9 pages.

* cited by examiner

METHOD, DEVICE AND COMPUTER-READABLE MEDIUM FOR AUTOMATICALLY CLASSIFYING CORONARY LESION ACCORDING TO CAD-RADS CLASSIFICATION BY A DEEP NEURAL NETWORK

FIELD

The present invention relates to a computer-implemented method for automatically detecting the presence or absence of a coronary lesion and classifying it by assigning a value as a function of its severity, using a deep neural network, as well as a device capable of automatically detecting the presence or absence of such coronary lesion and a non-transitory computer-readable medium storing computer-readable program instructions for automatically detecting the presence or absence of such coronary lesion.

BACKGROUND

Coronary disease is the second cause of mortality in the developed countries, after cancer. In particular, it affects more than fifteen millions of American. It can be revealed in a noisy manner, this is the first cause of sudden death in the world. About 50,000 case of sudden death per year in France, most by myocardial infarction. It can reach young subjects, sometimes in the groin. Its incidence increases with the aging of the population and the development of chronic diseases such as diabetes or arterial hypertension.

Cardiovascular diseases (MCV) regroup a number of disorders affecting the heart and blood vessels as:
  arterial hypertension (step-up of the voltage);
  coronary heart disease (heart attack or infarction);
  cerebrovascular diseases (stroke);
  peripheral arteriopathies;
  heart failure;
  rheumatic cardiopathies;
  congenital cardiopathies;
  cardiomyopathy.

Coronary cardiopathies also called coronary heart diseases, or coronary insufficiency, are obstructive diseases of the coronary arteries which vascularize the heart.

When it moves to stenosis (narrowing to occlusion), coronary artery injury results in coronary artery disease, or coronary artery disease, or coronary heart failure.

Coronary deficiencies generally result in myocardial ischemia, i.e., insufficient blood supply (ischemia) to the cardiac muscle (myocardial), in particular due to vascular obstruction.

Numerous complementary examinations allow to explore the myocardial ischemia, principal being electrocardiogram, strain proof, MRI, myocardial scintigraphy, coronarography, and more recently coronary angiography.

In practice, the classification of coronary stenoses according to their severity is most often performed visually in coronary angiography: it depends on one segmentation that relies on the extraction of the central line of the vessel. It is dependent on the experience of the reader. Stenosis is considered usually significant for a reduction in diameter of at least 50%, by visual estimation. This visual evaluation remains inaccurate with substantial inter-observer variability.

The accuracy in the classification of the degree of severity is very related to the image quality. The image quality depends on the heart rate, potential staircase artifacts between two beats, the quality of the contrast agent injection, the noise level in the image, and the possible presence of calcifications. The last cardiac scanning technology allows to obtain the best image quality on average by reducing most of the artefacts cited.

A long reading experience is necessary for the analysis of a coronary angio-scanner (Kerl et al, "64-*Slice Multidetector-Row Computer Tomograph in the Diagnosis of Coronary Artery Disease: Interview Agreement Among Radiologist With Varied Level of experience on Per-patient and Per-segment Basis*." J Thorac Imaging January 2012; 27 (1): 29-35).

These situations may lead to concluding to a coronary stenosis, sometimes causing a conventional, invasive and expensive angiography to be unnecessarily carried out.

Coronary angiography (or CCTA for Coronary CT angiography) is a recent, very sensitive method for the non-invasive detection of patients suspected of having a coronary artery disease with a very high negative predictive value (typically greater than 95%). Since the most sensitive method tends to be used in the screening of coronary diseases as first intention examination.

On the other hand, the coronary angiography has a least good specificity (about 50-70%) due to frequent false positives. Its positive predictive value of the scanner is therefore lower. The cases of false positives are observed in particular in the case of coronary calcifications and/or in the event of motion artifacts during the acquisition of the images. Thus, reading expertise is required to minimize the number of false positives. Good expertise is acquired in several years (5 years at minimum) for radiologists or cardiologists working in a dedicated center in cardiac imaging.

Document The SCOT-HEART Investors, "*Coronary CT Angiography and 5-Yeaar Rik of Myocardial Infarct*" N Engl J Med. 6 Sep. 2018 describes, in particular, that the use of coronary angiography can reduce the rate of infarct and mortality compared to a standard evaluation by a conventional force test.

However, the growing use of the coronary angiography is, in practice, braked by the level of expertise required for reliable interpretation in the current practice.

The arrival of artificial intelligence (AI) allows to envisage transferring certain elements of the medical expertise in algorithmic form. Machine Learning tools, and in particular the neural networks (NN), allow to reproduce expertise, which is very useful in the field of image recognition. Therefore, multiple projects are developed in the field of medical imaging.

Thus, the present invention includes adapting expertise in the reading of coronary angiography using the AI techniques The publication Zreik M et al, "*A Recurrent CNN for Automated detection and Classification of Coronary Artery Plate and Stenosis in Coronary CT Angiography*." I EEE Trans Med Imaging 2018 discloses a first method for automatic detection of stenoses by machine learning. However, this method uses only MPR images (for multiplanar reconstructions) stretched and not curvilinear, and analyzes the arteries by volume fragments, with a three-level classification (normal, less than 50% and greater than 50%) without automated evaluation of the image quality, and does not associate a functional evaluation.

Coronary angiography (CCTA) is a sensitive method for the detection of coronary lesions (plaque or stenosis), allowing in practice to spread out a coronary lesion when the examination is normal. Thus, automatic examination detection Normal (i.e. CAD-RADS 0 classified as CAD-RADS 0) could facilitate the physician's work which would concentrate on pathological cases, with a gain potential in reading time and in diagnostic performance.

The present invention relates to an automated determination of the value according to the CAD-RADS classification (Cury R C et al, "*Coronary Artery Disease-Reporting and Data System (CAD-RADS): An Expert Consensus Document of SCT, ACR and NCI: Assessed by the ACC.*" Cardioverter Cardiovasc Imaging 2016 September; 9 (9): 1099-1113) by using a first trained deep neural network applied directly to the detected images or portions of images secondarily refined by the use of other specifically trained neural networks:

- For the automatic prediction of the FFR (fractal flow reserve) at the threshold of 0.8 in the case of anatomically significant stenosis, that is to say in practice greater than 50%;
- For the automated determination of a calcification score having a prognostic value;
- For automated detection of a possible coronary plaque at acute risk cardiac event;
- For automated determination of the image quality to provide a diagnostic confidence index.

Finally, the document Nakanishi et al, "*Automated estimation of quality image for coronary computed tomography using machine learning.*" Eur Radiol. September 2018 describes the use of deep learning (deep learning) for the automatic evaluation of the image quality in CCTA (coronary or coronary angiography CT angiography). However, in this document, poor quality examinations were few due to an artificial preselection that does not correspond to daily practice. Moreover, in this document only axial, coronal and sagittal images were analyzed, but not MPR images.

Document Lossau et al, "*Motion artifact recognition and quantification in coronary CT angiograph using convolutional neural convolution.*" Med Image Anal. February 2019, also describes the use of deep learning for the automatic evaluation of the image quality in CCTA. This document discloses the feasibility of deep learning to quantify cardiac motion artifacts. On the other hand, in this document, the overall quality of the image is not analyzed (including noise, low contrast, or large calcifications). It is the overall quality of the image which allows to provide a diagnostic confidence index.

The present invention relates to a computer-implemented method for automatically detecting the presence or absence of a coronary lesion and classifying it by assigning a value of 0 to 5 as a function of its severity, according to the CAD-RADS classification (Coronary Artery Disease-Reporting and Data System value or System of reports and Data), using a neural network as well as a device capable of automatically detecting the presence or absence of a Coronary lesion and classifying it by assigning a value of 0 to 5 as a function of its severity, according to the CAD-RADS classification (for Coronary Artery Disease-Reporting and Data System value or System of reports and Data) using a neural network, and a non-transitory computer-readable medium storing computer-readable program instructions for automatically detecting the presence or absence of a coronary lesion and classifying it by assigning a value of 0 to 5 as a function of its severity, according to CAD-RADS classification, using a neural network.

The studies published in coronary angiography (CCTA or Coronary CT Angiography) rely on visual estimates of the stenoses, at the threshold of 50% in diameter, corresponding to the CAD-RADS classification 3, 4 or 5 (occlusion). The relevance of this detection is very dependent on the observer and its level of reading experience.

At this time, there is no reliable tool for the automatic detection of coronary lesions at the threshold of 50% available in current practice, due to the multiple factors interfering with the interpretation. These multiple factors are in particular the following: contrast, noise, cardiac or respiratory motion, anatomical variation, calcifications, which make the interpretation difficult.

The artificial intelligence techniques use statistical models capable of reproducing expertise, long to be acquired. By driving a neural network on thousands of images labeled by an expert, it is possible to approach the level of this expert without a priori modeling. Thus, it is possible to provide automatic detection of coronary stenosis with a performance close to that of an expert.

It is what the applicant was able to validate. The accuracy for detecting stenoses at the 50% threshold exceeds 90% in the validation data.

It is from this threshold of about 50% in diameter that a lesion is at risk of limiting the coronary flow. The stenosis is called in this significant case. Anatomically significant coronary stenosis is then speaking.

Beyond the detection of the stenosis at the threshold, it is very important to know whether the stenosis is hemodynamically significant or not. Indeed, only the stenoses which cause a pressure drop downstream of the stenosis must be treated mechanically by stent or possibly by coronary bypass.

This hemodynamic effect can be measured by measuring the pressure drop in maximum hyperemia. It is the basis of the calculation of the FFR.

Studies have shown that there is a benefit to mechanically treat patients with coronary stenosis only if the FFR is less than or equal to 0.8, translating a pressure drop downstream of the stenosis.

Therefore, it is important to be able to predict a level of FFR less than or equal to 0.8 in front of a coronary stenosis image. Such prediction would allow to avoid other more or less invasive examinations, expensive and the performance of which are not always perfectly correlated with the results of the invasive FFR.

If the FFR begins to drop for stenoses from 50%, it is recognized that the degree of stenosis on the image does not allow to correctly and reliably predict the value of the FFR.

Between 50 and 70% of stenosis, two thirds of the patients have FFR greater than 0.8, therefore their lesions are not in this case hemodynamically significant. Between 70 and 99% of stenosis, 80% of the patients have, on the other hand, an FFR of less than or equal to 0.8 (hemodynamically significant stenosis).

Thus, in the event of intermediate stenosis, that is to say comprised between 50 and 80%, it is difficult to know whether to treat or not the patient by a mechanical system (stent), or by bridging. Indeed, on this day, it is not possible to determine the hemodynamic character or not of a stenosis on the single anatomical imaging.

Other anatomical criteria have been proposed in the literature but do not appear to be sufficiently reliable to predict or not to predict a hemodynamic effect of a stenosis.

These anatomical criteria include, in particular, the degree of stenosis on the surface or in diameter, the minimum diameter, the minimum luminal surface, or the length of the stenosis. However, these anatomical criteria have not been studied in association but only in an isolated manner.

SUMMARY

The applicant has been able to emphasize that certain criteria associations were very relevant to determine the value of the FFR above or below the threshold of 0.8. This determination allows, in particular, to opt or not for a stent or bridge treatment.

In addition, direct learning of a second neural network from coronary stenoses images associated with FFR values, measured in vivo, also allows predicting an optional hemodynamic effect from the new images of coronary stenoses for which the FFR value is not known.

Considering what was mentioned above, a problem addressed by the present invention consists in limiting the interpretation variability between the observers of coronary stenoses linked to the expertise by determining the value according to the CAD-RADS classification directly on anatomical images.

The solution to this problem addressed is a computer-implemented method for determining the presence of a coronary lesion for a patient, comprising:

a step of receiving at least one curvilinear or stretched multiplanar medical image of computed tomography (X-scanner) of a coronary artery of said patient characterized in that it further comprises a step of determining a value according to the CAD-RADS classification of a coronary lesion on said image or on a portion of said image by using a first trained deep neural network applied directly to the detected images or portions of images.

It has a second object a device capable of determining the presence of a coronary lesion for a patient, comprising:

means for receiving at least one curvilinear or stretched multiplanar medical image of computed tomography (X-scanner), of a coronary artery of said patient;

characterized in that it further comprises means for determining a value according to the CAD-RADS classification of a coronary lesion on said image or on a portion of said image by using a first trained deep neural network applied directly to the detected images or portions of images.

Finally, the invention relates to a non-transitory computer-readable medium storing computer-readable program instructions for determining the presence of a coronary lesion for a patient, comprising execution by a computer-readable program instruction processor having the effect of performing the following operations:

receiving at least one curvilinear or stretched multiplanar medical image of computed tomography (X-scanner) of the coronary artery of said patient;

characterized in that it further generates, by said processor, an operation of determining a value according to the CAD-RADS classification of a coronary lesion on said image or on a portion of said image by using a first trained deep neural network applied directly to the detected images or portions of images.

The applicant has in particular been able to develop a method that has qualities for automatically detecting potentially significant coronary stenosis from a hemodynamic viewpoint (preferably CAD-RADS 3 or 4), based on high-level expertise. In contrast, the method also has the advantage of being able to predict the absence of coronary lesion by determining a CAD-RADS value 0 with a high probability. This system therefore allows, in a single examination of coronary angiography, to provide reliable results advantageously allowing to assist in the diagnosis and subsequently to adapt a therapeutic pipe.

BRIEF DESCRIPTION OF THE DRAWINGS

The invention and the advantages resulting therefrom will be better understood by reading the description and non-limiting embodiments which follow, illustrated in the accompanying drawings in which.

DETAILED DESCRIPTION

Figure 1:
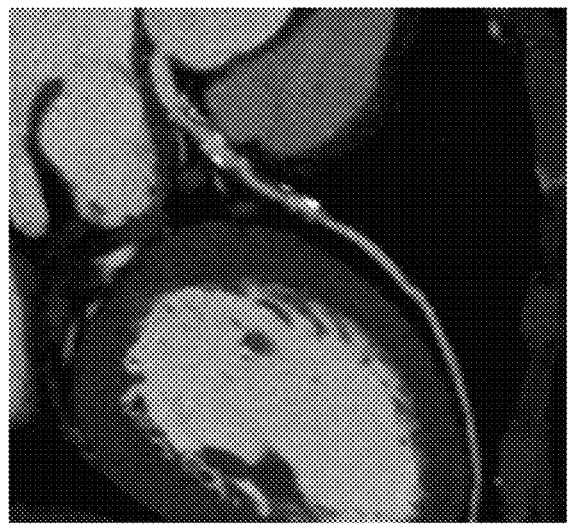
FIG. 1 shows a curvilinear MPR image having one stenosis.
Figure 2:
FIG. 2 shows a MPR image of a coronary artery having a stenosis.

A first object of the invention is a computer-implemented method for determining the presence or absence of a coronary lesion for a patient and classifying the severity of 0 (normal artery) to 5 (occluded artery).

The first step of said method is a step of receiving at least one curvilinear or stretched multiplanar medical image of computed tomography (X-scanner) of said patient including a coronary artery of interest. A multiplanar image is a reconstructed image from the centerline of a tubular anatomical structure such as a coronary artery. The major axis of the plane of the image is then aligned with the anatomical structure along this centerline. This allows to include the structure (here a coronary artery) in a single image. A MPR image may thus follow the curvilinear path of the vessel, and the adjacent structures are then distorted. The axis of the vessel may also be stretched by projection in a fixed direction. The visualization may take place on a 360° rotation axis in the two cases (curvilinear MPR or stretched MPR).

The second step of the method is a step of determining one value according to CAD-RADS classification (for Coronary Artery Disease-Reporting and Data System value or System of reports and Data) of a coronary lesion on said image or on a portion of said image by using a first trained deep neural network applied directly to the detected images or portions of images.

The images or parts of images are derived from Coronary angiography (or CCTA for Coronary Computer Tomograph Angiography).

The first neural network is trained to read curvilinear MPR images (multiplanar reconstructions), images alone or, for more diagnostic accuracy, multiple MPR images of the same artery viewed in several incidences, spaced at least 20°, preferably with a coverage of at least 180°. A basis of at least 5000, preferably 10 000 images of arteries has been analyzed and legal, with or without coronary or coronary damage, by an expert recognized with more than 20 years of experience of reading these images.

The curvilinear or stretched MPR images are obtained from the centerline of a coronary artery. This centerline is extracted by the current software on the radiological workstations, but it is sometimes necessary to correct the center line manually so that this line always remains well at the center of the circulating light. Each coronary artery is typically analyzed with multiple MPR by multiplying the incidences over 360°. This allows in particular to more easily detect asymmetric lesions, which may appear only under certain incidences.

A known method for automatic detection Zreik M et al, "*A Recurrent CNN for Automated detection and Classification* of Coronary Artery Plate and Stenosis in Coronary CT Angiography." IEEE Trans Med Imaging 2018 uses only the stretched MPR images, analyzing the fragments of manually annotated arteries, with a classification in three grades (normal, less than 50% and greater than 50%). This method does not analyze the artery in its entirety and does not analyze a same artery under multiple incidences over at least 180° as advantageously performed in the present invention. There is no automated evaluation of the FFR, the image quality, and the degree of overall calcification of an artery.

The method according to the invention therefore comprises a step of determining a value according to the CAD-RADS classification of a coronary lesion by using a first trained deep neural network applied directly to the detected images or portions of images.

Figure 6:
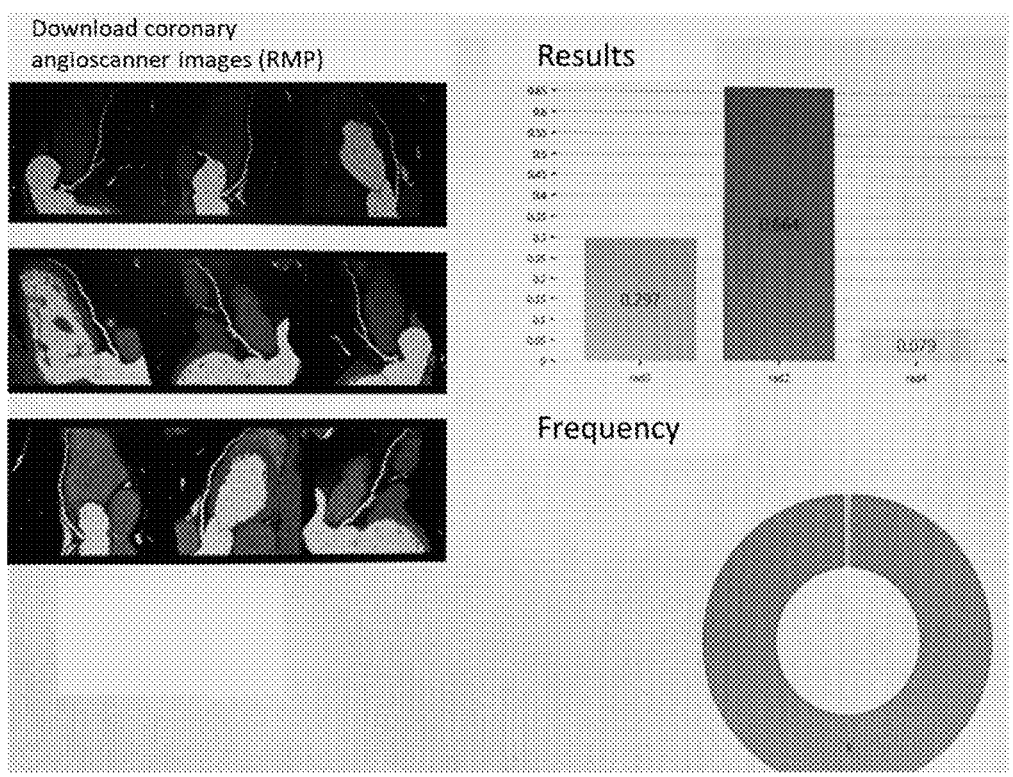
FIG. 6 illustrates an example of analysis of images of multiple incidences of the same artery analyzed by neural network.

FIG. 6 illustrates an example of analyzing images of multiple incidences of the same artery analyzed by neural network. The average of the probabilities by CAD-RADS classification of each image is calculated as well as the frequency of each classification.

A specific algorithm allows to classify a coronary artery according to CAD-RADS from multiple images. The algorithm, takes the most frequent classification of the images of different incidences (from 0 to 5), and compares it to the average of the probabilities of each classification. If the most frequent classification is also that with the highest average probability, it is retained by the algorithm. In the event of mismatch, it is the most severe ranking of the two which is retained: it is better in effect in clinical practice of screening a coronary lesion than the sub-estimate, in order to avoid false-negative examinations. The algorithm eliminates calculation of the probability scores below a certain decision threshold, in order to optimize the diagnostic performance of the neural network.

Thus, for example:

a/Nine MPR images of a same artery are classified by the neural network. Five MPR images are classified as CAD-RADS 4, two MPR images are classified as CAD-RADS 3, two MPR images are classified as CAD-RADS 2. The average probability CAD-RADS 4 is 0.8, that CAD-RADS 3 is 0.5, that of CAD-RADS 2 is 0.3. In this case, the lesion is classified as CAD-RADS 4 because this ranking is more frequent and its average probability is higher. The lesion will therefore be classified as CAD-RADS 4 with a probability of 0.8.

b/Nine MPR images of another artery are classified by the neural network. Five MPR images are classified as CAD-RADS 2, four MPR images are classified as CAD-RADS 3. The average probability CAD-RADS 2 is 0.6, that CAD-RADS 3 is 0.7. In this case, the lesion is classified CAD-RADS 3 because this ranking is most severe of 2. The lesion will be classified as CAD-RADS 3 with a probability of 0.7.

The CAD-RADS classification enables rational and uniformized classification of atheromatous coronary lesions. This classification in six degrees of severity (from 0 to 5) allows to propose optimal therapeutic choices for the patient with the light of the results of the coronary scanner (Cury R C et al, *"Coronary Artery Disease-Reporting and Data System (CA D-RADS): An Expert Consensus Document of SCT, ACR and NCI: Assessed by the ACC."* Cardioverter Cardiovasc Imaging. 2016 September; 9 (9): 1099-1113).

At this day, no automatic classification based on CAD-RADS was not proposed. Such automatic detection, which appears to be reliable on a first basis of 10000 images, can facilitate the daily work of interpretation of the radiologists or cardiologists, especially if they are little experienced.

CAD-RADS 0: normal
CAD-RADS 1: plaque<25%
CAD-RADS 2: plaque between 25 and 49%
CAD-RADS 3: 50-69% stenosis
CAD-RADS 4: 70-99% stenosis
CAD-RADS 5: occlusion Preferably, for a more reliable classification (precision>85%). categories 1 and 2 and categories 3 and 4 may be grouped as follows:
CAD-RADS 0: normal
CAD-RADS 1 or 2: non-obstructive coronary artery disease
CAD-RADS 3 or 4: obstructive coronary artery disease
CAD-RADS 5: occlusion Furthermore, advantageously, the method according to the invention further comprises a step of predicting a coronary fractal flow reserve interval by manual, semi-automated and/or automated measurement of at least two morphological criteria chosen from:

the degree of maximum coronary stenosis expressed in percentage (%) of diameter;
the degree of maximum coronary stenosis expressed in percentage (%) of surface;
the minimum diameter of the stenosis in mm;
the minimum surface area of the stenosis in $mm^2$;
the length of the stenosis in mm; and/or
the myocardial mass and the percentage (%) of myocardial mass downstream of the coronary stenosis.

Preferably, when the lesion is considered potentially significantly hemodynamically, then anatomical criteria are extracted from the image, manually, semi-automatic or automatic:

a: the minimum diameter of the stenosis in mm,
b: the minimum surface area of the stenosis in $mm^2$,
c: the degree of maximum coronary stenosis expressed in percentage (%) of diameter,
d: the degree of maximum coronary stenosis expressed in percentage (%) of surface,
e: the length of the stenosis in mm,
f: the myocardial mass and the percentage (%) of myocardial mass downstream of coronary stenosis.

By manually extracting the image, it must be understood a manual measurement of the diameter and the minimum surface of the vessel (on an artery section image) at the narrowest point of the stenosis; a manual drawing or contouring of the diameter and of the surface (on an artery section image), at a healthy artery segment closest to the stenosis; a manual measurement of the length; a visual estimate of the myocardial mass and the percentage of myocardial vascularized by an artery downstream of a stenosis on this same artery.

By semi-automatic extraction of the image, it must be understood a measure obtained by pre-creating centerlines from the pointing of a vessel by the user. At each point of the vessel, the values of the minimum diameter and the surface of the vessel are displayed by an algorithm on the radiological workstation. The various parameters of interest are readable at the area of interest with the possibility of manual correction of the centerlines and of the contours. Dedicated specific algorithms can calculate the vascularized myocardium volume downstream of a stenosis (according to the image processing software used).

By automatic extraction of the image, it must be understood a measurement obtained automatically by automatically creating the lines and contours of the vessel when loading images of a patient. The measurements are then automatically generated by software. At each point of the vessel, the values of the minimum diameter of the surface of the vessel are displayed by an algorithm on the radiological workstation. The various parameters of interest are readable at the area of interest with the possibility of manual correction of the centerlines and of the contours. Dedicated specific algorithms can calculate the vascularized myocardium volume downstream of a stenosis (according to the image processing software used).

Advantageously, the combination of at least two of these criteria and the neural network evaluation provides a prediction of the functional character by the FFR above or below the threshold of 0.8.

Preferably, the most relevant anatomical criteria for predicting an FFR value are:
the minimum surface area of the stenosis in mm$^2$ and
the degree of maximum coronary stenosis expressed in percentage (%) of surface.

More preferably still, the most relevant anatomical criteria for predicting an FFR value are
the minimum surface area of the stenosis in mm$^2$
the degree of maximum coronary stenosis expressed in percentage (%) of surface, and
the myocardial mass downstream of a stenosis.

Other criteria may also be used to predict an FFR value, it is the following criteria:
the minimum diameter of the stenosis in mm and
the degree of maximum coronary stenosis expressed in percentage (%) of diameter.

Figure 4:
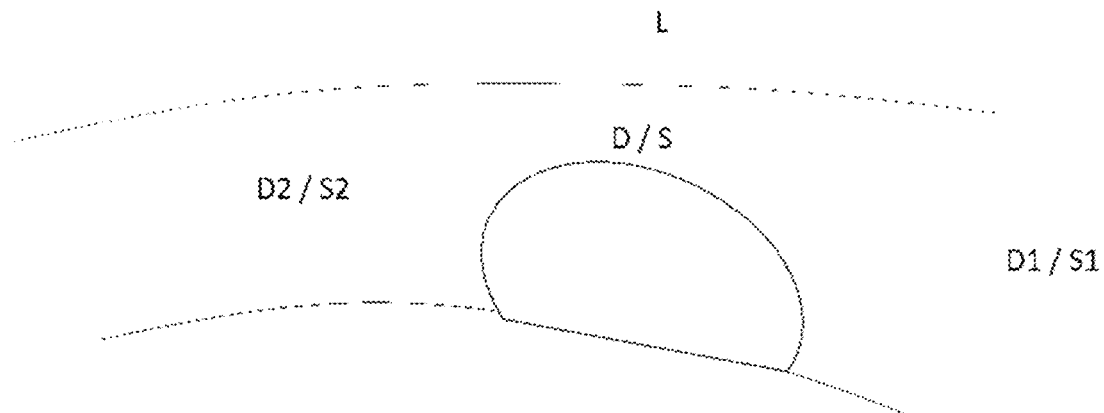
FIG. 4 shows some of the anatomical criteria allowing to predict whether a stenosis is hemodynamic or not.

As illustrated in FIG. 4, the anatomical criteria for qualifying a stenosis are:
Minimum diameter: D
Minimum area: S
Degree of stenosis in diameter: D/(D1-D2/2)
Surface stenosis degree: S/(S1-S2/2)
Stenosis length: L
Myocardial mass and percentage of myocardial mass downstream of a stenosis Also, the combination of at least two criteria allows to determine with one good precision if the FFR is less than 0.8.

The Applicant has been able to show that, on a sample of 120 stenoses, at least one of these combinations was in particular capable of completely separating lesions above or below the threshold of 0.83, value very close to the clinically validated threshold of 0.8.

Advantageously, the step of predicting a flow interval of the coronary fractal flow reserve further comprises the use of a second trained deep neural network, applied directly to the detected images or portions of images.

The second neural network is trained on reading curvilinear or stretched MPR images, images alone or for more precision of the multiple MPR images of the same stenosis according to several incidences, separated by at least 20°, covering at least 180°. The neural network was successfully trained on real images in which the actual value of FFR was measured.

A specific algorithm allows to predict the FFR of a given coronary artery from multiple images, at the threshold of 0.8. The algorithm, takes the most frequent classification of the images of different incidences, and compares it to the average of the probabilities of each classification. If the most frequent classification is also that with the highest average probability, it is retained by the algorithm. In the event of mismatch, it is the FFR+classification (FFR of less than or equal to 0.8) which is retained for the purpose of avoiding the maximum of false negative results, since it is considered to be more severe not to diagnose a more severe lesion than to overestimate a lesion in terms of screening.

Thus, for example:
a/Nine MPR images of a same artery with positive ranked stenosis "+" by the neural network are input to the algorithm. The latter finds five classified images FFR "+" and four classified images FFR "−". The average probability FFR "+" is 0.6, that FFR "−" is 0.5. In this case, the lesion is classified as FFR "+" (hemodynamically significant) because the FFR "+" ranking is more frequent and the average probability FFR "+" is higher. The lesion will be classified according to a probability of 0.6.

b/Nine other MPR images of a second artery with stenosis to be evaluated by the neuron network are input into the algorithm. Six are FFR "−" with an average probability of 0.9, the three others are FFR "+" with an average probability of 0.7. The ranking is more frequently FFR "−" with the highest probability. Stenosis is then judged to be hemodynamically significant (with high confidence).

c/a single MPR image of a third artery with stenosis to be evaluated is input into the algorithm. The image is considered to be FFR "−" by the neural network with an average probability of 0.6. The stenosis is judged not hemodynamically significant, but with a low confidence.

In the averaging calculations, the probability scores less than 0.2 are excluded because they are considered to be low discriminants by the neural network.

The result of this second neural network, if it confirms the first prediction on anatomical criteria, makes the prediction highly probable. In case of mismatch, the result of the FFR+overrides the prediction on the result FFR—because it is considered less serious in this clinical context of screening to overestimate a lesion than to underestimate it. The sensitivity for detecting hemodynamically significant lesions (FFR+) is thus preferred.

The method according to the invention advantageously comprises at least one of the following steps, which can be performed in any order:
a step of automated determination of the image quality providing a diagnostic confidence index by using a third neural network trained, applied directly to the detected images or portions of images;
a step of determining a global calcification score on a scale of 0 to 4 predicting the category of the Agatston calcium score, by using a fourth trained neural network, applied directly to the detected images or portions of images; and/or
a step of determining a high-risk plate (HRP) of a cardiac event, by using a fifth neural network trained, applied directly to the detected images or portions of images.

Excellent image quality is advantageous in order to obtain a reliable, relevant and accurate diagnosis in CCTA. The presence of artifacts, related to cardiac motion, at insufficient contrast, or noise in the image (the noise is measured as the standard deviation of the pixel values in a homogeneous region of an image), interfere with the diagnosis and severity of coronary stenosis and make the therapeutic decisions that follow more difficult. An automatic image quality assessment is useful for quality control, and for comparing the images from one center to the other. In the present invention, this automatic evaluation is advantageously used to provide a diagnostic confidence index in the final interpretation.

The third neural network for the step of automated determination of the image quality was successfully trained by supervised learning on MPR images of arteries whose image qualities were evaluated by a recognized expert. The images were classified according to a score of 0 to 4 according to the subjective scale (detailed below).

The neural network provides an overall image quality score from one to nine images of the same artery.

A specific algorithm allows to classify the image quality from images multiple of the same artery. The algorithm, takes the average of the classifications of the images of an artery according to different incidences (classified 0 to 4).

Thus, for example:

a/Nine MPR images of a same artery are classified by the neural network. Five MPR images are classified IQ 4, four MPR images are classified IQ 3.

The selected quality will be (5*4+4*3)/9=3.6. This number is, for example, considered as an indicator of the confidence for the final analysis.

The classification of the image quality is resumed below.

IQ=0. Non-evaluable
IQ=1. Low image quality. Artifact presence. Low diagnostic confidence
IQ=2. Correct. Interpretation is possible but the degree of confidence is low
IQ=3. Good IQ. Good diagnostic confidence
IQ=4. Excellent IQ. High degree of confidence The fourth network for the step of determining a global calcification score was trained directly on MPR images of arteries for which the Agatston calcium score was known by a prior scanner examination without contrast product injection; After training, the degree of calcification is semi-quantitatively predicted on an angiography injected according to four categories, for each of the extracted arteries:

0: No calcification
1: Moderate Calcifications: Agatston calcium score predicted between 1 and 99
2: Average Calcifications: Agatston calcium score predicted: between 100 and 400
3: Severe Calcifications: Agatston calcium score predicted: greater than 400.

The detection of coronary calcium is documented in the literature: in particular the Agatston calcium score is recognized as a large and independent risk marker for predicting the probability of coronary events, as well as risk factors known as the high level of cholesterol, diabetes or hypertension.

An algorithm retains the highest score on the images of a same artery according to multiple incidences, and then makes the sum of the scores obtained for each artery to obtain a global calcification score, allowing to predict a risk:

Sum=0 Agatston calcium score predicted: zero
Sum=1 Agatston calcium score predicted: 1-100
Sum=2 Agatston calcium score predicted: 100-200
Sum=3 Agatston calcium score predicted: 200-400
Sum>=4 Agatston calcium score predicted: >400

In the literature, the Agatston calcium score allows to estimate the risk of cardiovascular event at 10 years:

0: minimal risk,
Less than 100: low risk,
100-400: intermediate risk,
400: high risk.

According to the method of the invention, the actual calcium score is first calculated on a scanner without contrast injection, because the high-density contrast interferes with calcium and therefore does not allow calculation of the score. Machine learning was used to estimate the score automatically on contrast examinations, by learning from the score obtained on a scanner without contrast of the same patient.

Thus, for example:

For a given patient, five images are analyzed for each main artery (IVA for the anterior interventricular artery, Cx for the circumflex artery and RC for the right coronary)

The semi-quantitative calcium scores obtained by Artificial Intelligence are as follows:

IVA: 0, 0, 0, 0, 1
Cx: 1, 1, 1, 2, 1
RC: 0, 0, 0, 0, 0

Thus, the score $Ca = \text{Max}(IVA) + \text{Max}(Cx) + \text{Max}(RC)$ $= 1 + 2 + 0$ $= 3$ The score being 3, the Agatston calcium score predicted by the system will be between 200 and 400, corresponding to an intermediate risk.

Finally, the fifth network for the high-risk plate determination step was successfully trained by supervised learning on MPR images or section images of arteries, perpendicular to the MPR images, in which the possible presence of a vulnerable plaque was detected by a recognized expert. After training, the presence of a vulnerable plaque is asserted according to a probability threshold (between 0 and 1) calculated as the optimal threshold to obtain the best performance of this neural network. This performance is preferably measured using the area under the ROC curve (Receiver Operation Characteristic), with (1-Specificity) on the abscissa and sensitivity in ordinate.

The high-risk plates (HRP) are characterized by the presence of the following elements: low density plate (LDP), positive reshaping plate (RP) by increasing the vessel wall to the outside of the vessel, presence of a negative density zone within the plate (lipid core). The presence of at least two of the three first criteria allows to assert the presence of a high-risk plate.

There is no published system based on deep learning which automatically detects the risk plates from MPR images.

A specific algorithm allows to determine the presence of a vulnerable plaque. Due to its asymmetric character, it may be that a plate is not visible on one or more incidences of MPR images due to a different angle of view.

Thus, for example:

a/five MPR images of a same artery are analyzed by the neural network. The presence of a vulnerable plaque is denoted V, if the probability threshold reaches or exceeds 0.5, its absence is denoted by 0.

The result 0, 0, 0, V, 0 corresponds to the presence of a vulnerable plaque (because the presence was detected on at least one MPR image).

Figure 3:
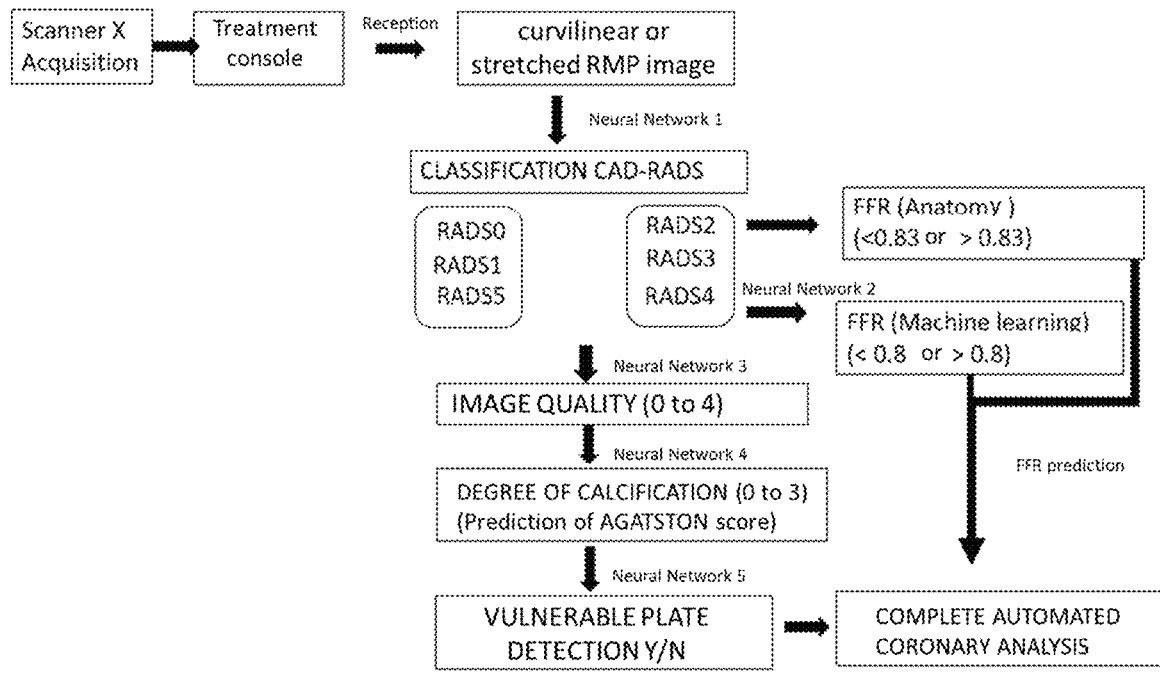
FIG. 3 is a functional diagram illustrating the various possible steps of a method according to the invention.

Preferably, as illustrated in FIG. 3, the method object of the invention comprises the following five steps which can be performed in any order:

a step of determining a value according to the CAD-RADS classification by using a first trained deep neural network applied directly to the detected images or portions of images;

a step of predicting a coronary fractal flow reserve interval by using a second trained deep neural network applied directly to the detected images or portions;

a step of automated determination of the image quality providing a diagnostic confidence index from a third trained neural network applied directly to the detected images or portions of images;

a step of determining a global calcification score on a scale of 0 to 4 predicting the Agatston calcium score, using a fourth trained neural network applied directly to the detected images or portions of images; and a step of determining a high-risk plate of a cardiac event, using a fifth trained neural network applied directly to the detected images or portions of images.

Preferably, the detection of images or portions of images corresponding to the lesion of the patient of the method according to the invention comprises detecting portions of images corresponding to the coronary lesion, a coronary tree, coronary ostia, or coronary vessels.

The invention also relates to a device capable of determining the presence of a coronary lesion for a patient, comprising means for receiving at least one curvilinear or stretched multiplanar medical image of computed tomography (X-scanner), of a coronary artery of said patient; said device further comprises means for determining a value according to the CAD-RADS classification of a coronary lesion on said image or on a portion of said image by using a first trained deep neural network applied directly to the detected images or portions of images.

The first neural network is as described above.

Preferably, the device further comprises means for predicting a coronary fractal flow reserve interval by using a second trained deep neural network applied directly to the detected images or portions of images.

The second neural network is as described above.

Advantageously, the device according to the invention further comprises at least one of the following means:
    means for automated determination of the image quality providing a diagnostic confidence index by using a third trained neural network applied directly to the detected images or portions of images;
    means for determining a global calcification score on a scale of 0 to 4 predicting the Agatston calcium score, by using a fourth trained neural network applied directly to the detected images or portions of images; and/or
    means for determining a high-risk plate of a cardiac event, by using a fifth network of trained neurons applied directly to the detected images or portions of images.

The third, fourth and fifth neural networks are as described above.

According to a preferred embodiment of the invention, the device comprises the following five means:
    means for determining a value according to the CAD-RADS classification by using a first trained deep neural network applied directly to the detected images or portions of images;
    means for predicting a coronary fractal flow reserve interval by using a second trained deep neural network applied directly to the detected images or portions;
    means for automated determination of the image quality providing a diagnostic confidence index by using a third trained neural network applied directly to the detected images or portions of images;
    means for determining a global calcification score on a scale of 0 to 4 predicting the Agatston calcium score, by using a fourth trained neural network applied directly to the detected images or portions of images; and
    means for determining a high-risk plate of a cardiac event, by using a fifth network of trained neurons applied directly to the detected images or portions of images.

Finally, the invention relates to a non-transitory computer-readable medium storing computer-readable program instructions for determining the presence of a coronary lesion for a patient, comprising the execution by a computer-readable program instruction processor having the effect of performing the following operations:
    receiving at least one curvilinear or stretched multiplanar medical image of computed tomography (X-scanner) of the coronary artery of said patient;
characterized in that it further generates, by said processor, an operation of determining a value according to the CAD-RADS classification of a coronary lesion on said image or on a portion of said image by using a first trained deep neural network applied directly to the detected images or portions of images.

Preferably, the support is able to further generate the implementation by said processor of a prediction operation of a coronary fractal flow reserve interval by using a second trained deep neural network applied directly to the detected images or portions of images.

More preferably, the support is able to further generate, by said processor, at least one of the following operations:
    automated determination of image quality providing a diagnostic confidence index by using a third trained neural network applied directly to the detected images or portions of images;
    determination of a global calcification score on a scale of 0 to 4 predicting the Agatston calcium score, by using a fourth trained neural network applied directly to the detected images or portions of images; and/or
    determining a high-risk plate of a cardiac event, by using a fifth trained neural network applied directly to the detected images or portions of images.

According to a preferred embodiment of the invention, the support generates the performing by said processor of the following five operations:
    determining a value according to the CAD-RADS classification by using a first trained deep neural network applied directly to the detected images or portions;
    predicting a coronary fractal flow reserve interval by using a second trained deep neural network applied directly to the detected images or portions;
    automated determination of the image quality providing a diagnostic confidence index by using a third trained neural network applied directly to the detected images or portions of images;
    determining a global calcification score on a scale of 0 to 4 predicting the Agatston calcium score of, by using a fourth trained neural network applied directly to the detected images or portions of images; and
    determining a high-risk plate of a cardiac event, by using a fifth trained neural network applied directly to the detected images or portions of images.

The present invention will now be illustrated by means of the following examples:

Example 1

A wide database of more than 10 000 MPR images from coronary angiography was used for supervised learning. All images were classified and labeled by an expert with more than 20 years of reading experience of these images (corresponding to about 50,000 cases analyzed). The images of this base were classified in terms of image quality, degree of calcification, and degree of stenosis as a function of CAD-RADS classification. The possible presence of risk plate (vulnerable plate) has been specified. Moreover, on 4500 images of patients with stenosis and known FFR value, a binary classification at the threshold FFR of 0.8 was performed. A neural network could thus be trained to predict on a new image if the FFR value will be higher or lower (> or <) to 0.8.

Different networks of available neurons in free access were tested, for example: GOODGLENET™, RESNET™, and INCEPTION™ V3, VGG11™, VGG13™, VGG19™, in order to obtain the best classification rate. Various measurements were made on a test database, independent of the learning base: precision calculations of the test, of the sensitivity, of the specificity, of the positive predictive value, of the negative predictive value, of the score F1 (harmonic mean between the sensitivity and the positive predictive value), of the area under the curve ROC.

The MPR multiplanar images are provided from the base by the scanner consoles of all different scanner manufacturers from the centerlines. Generally, curvilinear or stretched MPR images, and one to nine images of the same artery. The images may be exported from the workstations in a DICOM or other X-ray standard image format (eg, JPEG, PNG . . . ), and secondarily loaded on a dedicated Internet site. They may also be directly loaded on an Internet site from the workstation. The evaluation result produced is then returned to the usual environment of the reader.

Example 2: Creation of Neural Networks, Methods and Results

A wide base of stretched or curvilinear MPR image data was created from examinations performed on a scanner 64 cross-sections, a scanner 256 cross-sections, and a scanner 320 cross-sections in four different institutions.

The patient data has been anonymized.

For each data set, the MPR images of the three main arteries have been extracted: IVA, the circumflex artery, and the right coronary artery.

For each of the three arteries, nine images were selected with different angles of view (with 20° of minimum deviation, for a total coverage of 180° minimum), by rotation around the central line.

Each MPR image was classified by an expert in view of the image quality, the degree of calcification, the presence or absence of a vulnerable plaque, and its degree of stenosis using the CAD-RADS classification.

A reduced database of 4500 images on 500 patients with a known FFR value was also driven.

The images were loaded on a platform (DEEPOMTIC™ STUDIO, Paris, France, CLEVERDOC™ Lille, France) for classifying the images and testing the different neural networks.

For each neural network, 80% of the images of the database were used for training, and 20% of the images were used for evaluation. The evaluation images have been excluded from the training process.

For each task, different neural networks have been used for training.

The networks associated with the best results (better sensitivity, better positive predictive value, better score F1, or better area under the curve) have been selected.

Results and Conclusion

For the automatic detection of the vulnerable plaques, the average score F1 has reached 70%.

For the automatic calcium score, the average score F1 reaches 75%.

For the automatic classification of the image quality, the score F1 reaches 75%.

For the classification of the stenoses into 4 CAD-RADS classes the area under the curve reaches 88%.

Figure 5:
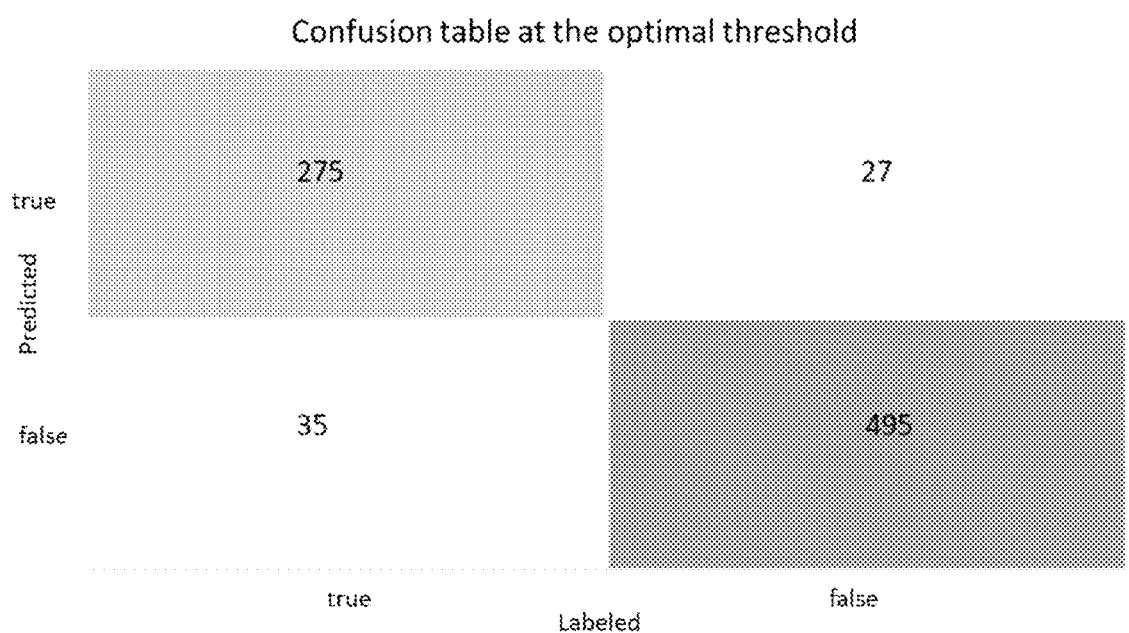
FIG. 5 shows results of CAD-RADS detection 0 by the neural network.

FIG. 5 illustrates the results of CAD-RADS 0 detection by the neural network. At the optimal decision threshold of 0.55, the detection sensitivity of the normal arteries (CAD-RADS 0) is 275/275+35 or 89%. The specificity for it is 495/495+27 or 95%. The neural network thus appears very well to determine the normal arteries also, allowing to prioritize the reading of the examinations according to the degree of severity determined automatically.

For the prediction of an FFR value less than or equal to 0.8, the average F1 score reaches 87%.

The results obtained on this first base therefore appear equal to or greater than those of the other methods which are more complex to implement and more expensive. This technique allows to provide a diagnostic and therapeutic immediate decision tool.

The invention claimed is:

1. A computer-implemented method for determining the presence of a coronary lesion for a patient, comprising:
   receiving at least one curved or stretched multiplanar medical image of computed tomography (X-scanner) of a coronary artery of said patient; and
   determining a value according to the CAD-RADS classification (for Coronary Artery Disease-Reporting and Data System value or System of reports and Data) of a coronary lesion on said image or on a portion of said image by using a first trained deep neural network applied directly to the detected images or portions of detected images.

2. The method according to claim 1, further comprising predicting a coronary fractal flow reserve interval (FFR) by manual, semi-automated and/or automated measurement of at least two morphological criteria selected from:
   the degree of maximum coronary stenosis expressed in percentage (%) of diameter;
   the degree of maximum coronary stenosis expressed in percentage (%) of surface;
   the minimum diameter of the stenosis in mm;
   the minimum surface area of the stenosis in mm$^2$;
   the length of the stenosis in mm; or
   the myocardial mass and the percentage (%) of myocardial mass downstream of the coronary stenosis.

3. The method according to claim 1, further comprising predicting a coronary fractal flow reserve interval of coronary stenosis by using a second trained deep neural network applied directly to the detected images or portions of images.

4. The method according to claim 1, further comprising at least one of the following:
   automated determination of the image quality providing a diagnostic confidence index by using a third trained neural network applied directly to the detected images or portions of detected images;
   determining a global calcification score on a scale of 0 to 4 predicting the Agatston calcium score, by using a fourth trained neural network applied directly to the detected images or portions of images; and/or
   determining a high-risk plaque (HRP) of a cardiac event, by using a fifth trained neural network applied directly to the detected images or portions of detected images.

5. The method according to claim 4, further comprising:
   determining a value according to the CAD-RADS classification by using a first trained deep neural network applied directly to the detected images or portions;
   predicting a coronary reserve flow value interval by using a second trained deep neural network applied directly to the detected images or portions;
   automated determination of the image quality providing a diagnostic confidence index from a third trained neural network applied directly to the detected images or portions of detected images;

determining a global calcification score on a scale of 0 to 4 predicting the Agatston calcium score, by using a fourth trained neural network applied directly to the detected images or portions of detected images; and determining a high-risk plaque of a cardiac event, using a fifth trained neural network applied directly to the detected images or portions of detected images.

6. The method according to claim 5, wherein the detection of images or portions of images corresponding to the lesion of the patient comprises detecting portions of images corresponding to the coronary lesion, a coronary tree, coronary ostia, or coronary vessels.

7. The method according to claim 1, wherein the images or portions of images are derived from a Coronary angiography (or CCTA: for Coronary Computer Tomograph Angiography).

8. A device adapted to determine the presence of a coronary lesion for a patient, comprising:
at least one input adapted to receiving at least one curved or stretched multiplanar medical image of computed tomography (X-scanner), of a coronary artery of said patient; at least one processor configured for determining a value according to the CAD-RADS classification (for Coronary Artery Disease-Reporting and Data System value or System of reports and Data) of a Coronary lesion on said image or on a portion of said image by using a first trained deep neural network applied directly to the detected images or portions of images.

9. The device according to claim 8, wherein the at least one processor is further configured for predicting a coronary reserve flow value interval by using a second trained deep neural network applied directly to the detected images or portions of detected images.

10. The device according to claim 8, wherein the at least one processor is further configured for:
automated determination of the image quality providing a diagnostic confidence index by using a third trained neural network applied directly to the detected images or portions of detected images;
determining a global calcification score on a scale of 0 to 4 predicting the Agatston calcium score, by using a fourth trained neural network applied directly to the detected images or portions of detected images; and/or
determining a high-risk plaque of a cardiac event, by using a fifth trained neural network applied directly to the detected images or portions of detected images.

11. The device according to claim 10, wherein the at least one processor is further configured for:
determining a value according to the CAD-RADS classification by using a first trained deep neural network applied directly to the detected images or portions;
predicting a coronary reserve flow value interval by using a second trained deep neural network applied directly to the detected images or portions;
automated determination of the image quality providing a diagnostic confidence index by using a third trained neural network applied directly to the detected images or portions of images;
determining a global calcification score on a scale of 0 to 4 predicting the Agatston calcium score, by using a fourth trained neural network applied directly to the detected images or portions of detected images; and
determining a high-risk plaque of a cardiac event, by using a fifth trained neural network applied directly to the detected images or portions of detected images.

12. A non-transitory computer-readable medium storing computer-readable program instructions for determining the presence of a coronary lesion for a patient, comprising executing by a computer-readable program instruction processor having the effect of performing the following operations:
receiving at least one curved or stretched multiplanar medical image of computed tomography (X-scanner) of the coronary artery of said patient;
wherein it further generates by said processor an operation of determining a value according to the CAD-RADS classification (for Coronary Artery Disease-Reporting and Data System value or System of reports and Data) of a Coronary lesion on said image or on a portion of said image by using a first trained deep neural network applied directly to the detected images or portions of detected images.

13. The non-transitory computer-readable medium according to claim 12, wherein it further generates by said processor a prediction operation of a coronary reserve flow value interval by using a second trained deep neural network applied directly to the detected images or portions of detected images.

14. The non-transitory computer-readable medium according to one of claim 13, wherein it further generates, by said processor, at least one of the following operations:
automated determination of an image quality providing a diagnostic confidence index by using a third trained neural network applied directly to the detected images or portions;
determination of a global calcification score on a scale of 0 to 4 predicting the Agatston calcium score, by using a fourth trained neural network applied directly to the detected images or portions of detected images; and/or
determination of a high-risk plaque of a cardiac event, by using a fifth trained neural network applied directly to the detected images or portions of images.

15. The non-transitory computer-readable medium according to claim 14, wherein it generates the execution by said processor of the following five operations:
determining a value according to the CAD-RADS classification by using a first trained deep neural network applied directly to the detected images or portions or detected images;
predicting a coronary reserve flow value interval by using a second trained deep neural network applied directly to the detected images or portions of detected images;
automatically determining the image quality providing a diagnostic confidence index by using a third trained neural network applied directly to the detected images or portions of detected images;
determining a global calcification score on a scale of 0 to 4 predicting the Agatston calcium score, by using a fourth trained neural network applied directly to the detected images or portions of detected images; and
determining a high-risk plaque of a cardiac event, by using a fifth trained neural network applied directly to the detected images or portions of detected images.

16. The non-transitory computer-readable medium according to one of claim 12, wherein it further generates, by said processor, at least one of the following operations:
automated determination of an image quality providing a diagnostic confidence index by using a third trained neural network applied directly to the detected images or portions;
determination of a global calcification score on a scale of 0 to 4 predicting the Agatston calcium score, by using a fourth trained neural network applied directly to the detected images or portions of detected images; and/or determination of a high-risk plaque of a cardiac event, by using a fifth trained neural network applied directly to the detected images or portions of images.

17. The non-transitory computer-readable medium according to claim 16, wherein it generates the execution by said processor of the following five operations:

determining a value according to the CAD-RADS classification by using a first trained deep neural network applied directly to the detected images or portions or detected images;

predicting a coronary reserve flow value interval by using a second trained deep neural network applied directly to the detected images or portions of detected images;

automatically determining the image quality providing a diagnostic confidence index by using a third trained neural network applied directly to the detected images or portions of detected images;

determining a global calcification score on a scale of 0 to 4 predicting the Agatston calcium score, by using a fourth trained neural network applied directly to the detected images or portions of detected images; and determining a high-risk plaque of a cardiac event, by using a fifth trained neural network applied directly to the detected images or portions of detected images.

* * * * *